United States Patent
Berner et al.

(10) Patent No.: US 7,612,103 B2
(45) Date of Patent: Nov. 3, 2009

(54) PLEUROMUTILIN DERIVATIVES AS ANTIMICROBIALS

(75) Inventors: Heinz Berner, Vienna (AT); Gabriele Kerber, Vienna (AT)

(73) Assignee: Nabriva Therapeutics AG, Vienna (AT)

( * ) Notice: Subject to any disclaimer, the term of this patent is extended or adjusted under 35 U.S.C. 154(b) by 612 days.

(21) Appl. No.: 10/521,926

(22) PCT Filed: Jul. 23, 2003

(86) PCT No.: PCT/EP03/08059

§ 371 (c)(1), (2), (4) Date: Jul. 22, 2005

(87) PCT Pub. No.: WO2004/011431

PCT Pub. Date: Feb. 5, 2004

(65) Prior Publication Data

US 2005/0250811 A1   Nov. 10, 2005

(30) Foreign Application Priority Data

| Jul. 24, 2002 | (GB) | ................... 0217149.4 |
| Jul. 25, 2002 | (GB) | ................... 0217305.2 |
| Mar. 27, 2003 | (WO) | ............ PCT/EP03/08059 |

(51) Int. Cl.
- A61K 35/31 (2006.01)
- A31K 35/27 (2006.01)
- C07D 211/80 (2006.01)

(52) U.S. Cl. ................ 514/355; 514/423; 514/476; 546/285

(58) Field of Classification Search ............ 546/285; 514/355, 423, 476
See application file for complete search history.

(56) References Cited

U.S. PATENT DOCUMENTS

| 6,281,226 B1 | 8/2001 | Sanderson et al. |
| RE39,128 E * | 6/2006 | Berry et al. ............. 514/305 |
| 7,169,804 B2 * | 1/2007 | Ascher et al. ............ 514/423 |

FOREIGN PATENT DOCUMENTS

| WO | 01/09095 | 2/2001 |
| WO | 02/12199 | 2/2002 |
| WO | 02/22580 | 3/2002 |

* cited by examiner

*Primary Examiner*—Janet L. Andres
*Assistant Examiner*—Raymond Covington
(74) *Attorney, Agent, or Firm*—D. Peter Hochberg; Sean F. Mellino; Daniel J. Smola

(57) ABSTRACT

Compounds of formula

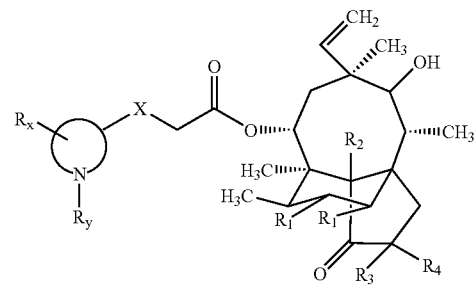

wherein
$R_1$ and $R_1'$ are hydrogen or deuterium,
$R_2$, $R_3$ and $R_4$ are hydrogen or deuterium,
$R_5$ is the residue of an amino acid,
X is S or N-ALK,

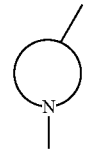

is piperidinyl or tetrahydropyridinyl,
ALK is $(C_{1-4})$alkyl, and
$R_6$ is hydrogen, hydroxy or $(C_{2-12})$acyloxy,
and their use as antimicrobials.

8 Claims, No Drawings

PLEUROMUTILIN DERIVATIVES AS ANTIMICROBIALS

The present invention relates to pleuromutilins having pharmaceutical, e.g. antimicrobial, activity.

In one aspect the present invention provides a compound of formula

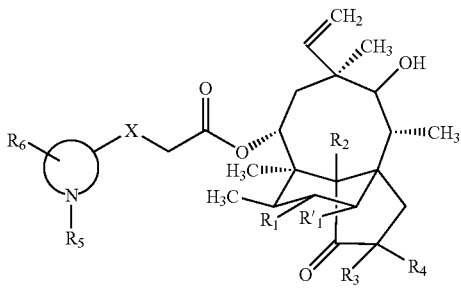

wherein
$R_1$ and $R_1'$ are hydrogen or deuterium,
$R_2$, $R_3$ and $R_4$ are hydrogen or deuterium,
$R_5$ is the residue of an amino acid, e.g. a valyl or histidinyl residue,
X is S or N-ALK,

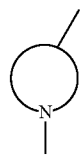

is piperidinyl or tetrahydropyridinyl,
ALK is $(C_{1-4})$alkyl, e.g. methyl, and
$R_6$ is hydrogen, hydroxy or $(C_{2-12})$acyloxy, e.g. $(C_{2-6})$alkylcarbonyloxy, e.g. —O—CO—CH$_3$, with the proviso that if

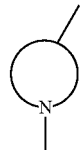

is piperidinyl and X is S, then $R_6$ is other than hydrogen.

In another aspect the present invention provides a compound of formula I, wherein
$R_1$, $R_1'$, $R_2$, $R_3$ and $R_4$ are hydrogen,
$R_5$ is the residue of an amino acid, e.g. a valyl or histidinyl residue,
X is S,

is piperidinyl or tetrahydropyridinyl, and
$R_6$ is hydroxy.

In another aspect the present invention provides a compound of formula I, wherein
$R_1$, $R_1'$, $R_2$, $R_3$ and $R_4$ are hydrogen,
$R_5$ is a residue of an amino acid, e.g. valyl or histidinyl,
X is N-ALK,

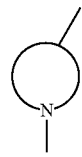

is piperidinyl,
ALK is $(C_{1-4})$alkyl, e.g. methyl, and
$R_6$ is hydroxy.

In another aspect the present invention provides a compound of formula I selected from the group consisting of
14-O-[4-hydroxy-N-valyl-piperidin-3-yl]-sulfanylacetylmutilin, such as 14-O-[4-hydroxy-N—(R)-valyl-piperidin-3-yl]-sulfanylacetylmutilin, e.g. in the form of a hydrochloride,
14-O-[3-hydroxy-N-valyl-piperidin-4-yl]-sulfanylacetylmutilin, such as 14-O-[3-hydroxy-N—(R)-valyl-piperidin-4-yl]-sulfanylacetylmutilin, e.g. in the form of a hydrochloride,
14-O-[3-hydroxy-N-histidinyl-piperidin-4-yl]-sulfanylacetylmutilin, such as 14-O-[3-hydroxy-N—(R)-histidinyl-piperidin-4-yl]-sulfanylacetylmutilin, e.g. in the form of a dihydrochloride,
14-O-[3-hydroxy-N-valyl-piperidin-4-yl]-methylaminoacetylmutilin, such as 14-O-[3-hydroxy-N—(R)-valyl-piperidin-4-yl]-methylaminoacetylmutilin, e.g. in the form of a dihydrochloride,
14-O-[4-hydroxy-N-valyl-piperidin-3-yl]-methylaminoacetylmutilin, such as 14-O-[4-hydroxy-N—(R)-valyl-piperidin-3-yl]-methylaminoacetylmutilin, e.g. in the form of a dihydrochloride,
14-O-[N-valyl)-1,2,3,6-tetrahydropyridin-3-yl]-sulfanylacetylmutilin, such as 14-O-[N—(R)-valyl-1,2,3,6-tetrahydropyridin-3-yl]-sulfanylacetylmutilin, and
14-O-[N-valyl)-1,4,5,6-tetrahydropyridin-4-yl]-sulfanylacetylmutilin, such as 14-O-[N—(R)-valyl-1,4,5,6-tetrahydropyridin-4-yl]-sulfanylacetylmutilin.

Compounds of formula I may be prepared by splitting off a protecting group from compounds of formula I wherein functional groups, e.g. amino groups, are protected. Such compounds may be thus useful as intermediates in the production of a compound of formula I, or may be pharmaceutically active.

In another aspect the present invention provides a compound of formula

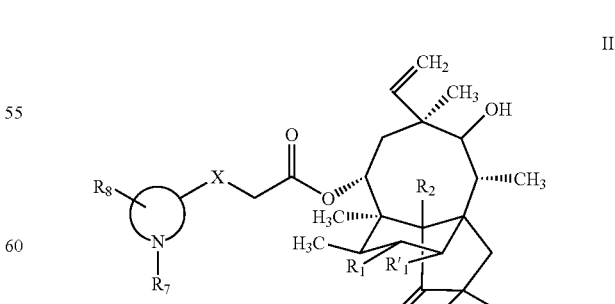

wherein
$R_1$ and $R_1'$ are hydrogen or deuterium, $R_2$, $R_3$ and $R_4$ are hydrogen or deuterium,
$R_7$ is a protecting group, e.g. BOC, or the residue of an amino acid wherein the amino group is protected, e.g. N-BOC protected valyl or histidinyl,
X is S or N-ALK,

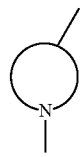

is piperidinyl or tetrahydropyridinyl,
ALK is $(C_{1-4})$alkyl, e.g. methyl, and
$R_8$ is hydrogen, hydroxy or $(C_{2-12})$acyloxy, e.g. $(C_{2-6})$alkyl-carbonyloxy, e.g. —O—CO—$CH_3$, with the proviso that if

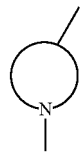

is piperidinyl and X is S, then $R_8$ is other than hydrogen.

BOC as used herein is tert.butoxycarbonyl.

In another aspect the present invention provides a compound of formula II, wherein
$R_1$, $R_1'$, $R_2$, $R_3$ and are hydrogen,
$R_7$ is tert.butoxycarbonyl or the residue of an amino acid wherein the amino group is protected by tert.butoxycarbonyl, e.g. N-BOC protected valyl or histidinyl,
X is S or N-ALK,

is piperidinyl or tetrahydropyridinyl,
ALK is $(C_{1-4})$alkyl, e.g. methyl, and
$R_8$ is hydrogen, hydroxy or acetoxy, with the proviso that if

is piperidinyl and X is S, then $R_8$ is other than hydrogen.

Protecting group include protecting groups which may be, e.g. selectively, removed, if desired, and include protecting groups which are conventional in chemistry, e.g. (pleuro) mutilin chemistry, preferably BOC, e.g. which BOC can be removed e.g. by treatment with etheric HCl.

In another aspect the present invention provides a compound of formula II selected from the group consisting of
14-O—[N-BOC-4-hydroxy-piperidin-3-yl]-sulfanylacetylmutilin,
14-O—[N-BOC-3-hydroxy-piperidin-4-yl]-sulfanylacetylmutilin,
14-O-[4-hydroxy-N-BOC-piperidin-3-yl]-methylaminoacetylmutilin,
14-O-[3-hydroxy-N-BOC-piperidin-4-yl]-methylaminoacetylmutilin,
14-O—[N-BOC-1,4,5,6-tetrahydropyridin-4-yl]-sulfanylacetylmutilin, such as 14-O—[N-BOC-1,4,5,6-tetrahydropyridin-4(R*)-yl]-sulfanylacetylmutilin and 14-O—[N-BOC-1,4,5,6-tetrahydropyridin-4(S*)-yl]-sulfanylacetylmutilin,
14-O-[4-hydroxy-N—(N-BOC-valyl)-piperidin-3-yl]-sulfanylacetylmutilin, such as 14-O-[4-hydroxy-N—(N-BOC-(R)-valyl)-piperidin-3-yl]-sulfanylacetylmutilin, e.g. in the form of a hydrochloride,
14-O-[3-hydroxy-N—(N-BOC-valyl)-piperidin-4-yl]-sulfanylacetylmutilin, such as 14-O-[3-hydroxy-N—(N-BOC-(R)-valyl)-piperidin-4-yl]-sulfanylacetylmutilin, e.g. in the form of a hydrochloride,
14-O-[4-acetoxy-N—(N-BOC-valyl)-piperidin-3-yl]-sulfanylacetylmutilin, such as 14-O-[4-acetoxy-N—(N-BOC-(R)-valyl)-piperidin-3-yl]-sulfanylacetylmutilin, e.g. in the form of a hydrochloride,
14-O-[3-acetoxy-N—(N-BOC-valyl)-piperidin-4-yl]-sulfanylacetylmutilin, such as 14-O-[3-acetoxy-N—(N-BOC-(R)-valyl)-piperidin-4-yl]-sulfanylacetylmutilin, e.g. in the form of a hydrochloride,
14-O-[3-hydroxy-N—(N-BOC-histidinyl)-piperidin-4-yl]-sulfanylacetylmutilin, such as 14-O-[3-hydroxy-N—(N-BOC-(R)-histidinyl-piperidin-4-yl]-sulfanylacetylmutilin, e.g. in the form of a dihydrochloride.
14-O-[3-hydroxy-N—(N-BOC)-valyl-piperidin-4-yl]-methylaminoacetylmutilin, such as 14-O-[3-hydroxy-N—(N-BOC)-(R)-valyl-piperidin-4-yl]-methylaminoacetylmutilin, e.g. in the form of a dihydrochloride,
14-O-[4-hydroxy-N—(N-BOC)-valyl-piperidin-3-yl]-methylaminoacetylmutilin, such as 14-O-[4-hydroxy-N—(N-BOC)-(R)-valyl-piperidin-3-yl]-methylaminoacetylmutilin, e.g. in the form of a dihydrochloride,
14-O—[N—(N-BOC-valyl)-1,4,5,6-tetrahydropyridin-4-yl]-sulfanylacetylmutilin, such as 14-O—[N—(N-BOC-(R)-valyl)-1,4,5,6-tetrahydropyridin-4-yl]-sulfanylacetylmutilin,
14-O—[N—(N-BOC-valyl)-1,2,3,6-tetrahydropyridin-3-yl]-sulfanylacetylmutilin, such as 14-O—[N—(N-BOC-(R)-valyl)-1,2,3,6-tetrahydropyridin-3-yl]-sulfanylacetylmutilin.

In a compound of formula I or of formula II the group X may be attached to the piperidine or tetrahydropyridine ring in any position with the exception of position 1, e.g. in position 2, 3, 4, 5 or 6, preferably in position 3 or 4. In a compound of formula I or of formula II, the group I, $R_6$, or the group $R_8$ respectively, may be in any position with the exception of position 1, of the piperidine or tetrahydropyridine ring, e.g. in position 2, 3, 4, 5 or 6, preferably in position 3 or 4. $R_8$ preferably is alkyl, e.g. $(C_{1-20})$alkyl, when in position 2 or 6. In a preferred group of compounds of formula I or of formula II the group X is in position 3 or in position 4; and $R_6$, or the group $R_8$ respectively, is in position 3 or in position 4.

In a compound of formula I or of formula II each single substituent may be a preferred substituent, e.g. independently of each other substituent defined.

"A residue of an (N-protected) amino acid" as used herein means that in a compound of formula I or of formula II the carbonyl group of said (protected) amino acid is bound to the nitrogen of the group of formula

and the —OH group of said amino acid function is missing, i.e. the N of the ring is acylated by the carboxylic group of an amino acid. Preferably the residue of an (N-protected)-amino acid is the residue of an (N-protected)-α-amino acid, e.g. a naturally occurring α-amino acid, e.g. (N-protected)-valyl or (N-protected)-histidinyl, preferably (N-protected)-R-valyl.

Compounds provided by the present invention, e.g. a compound of formula I or of formula II, are hereinafter designated as "compound(s) of (or compound(s) according to) the present invention". A compound of the present invention includes a compound in any form, e.g. in free form, in the form of a salt, in the form of a solvate and in the form of a salt and a solvate. Compounds of formula II are useful intermediates in the preparation of compounds of formula I. Compounds of formula II also may show, however, pharmaceutical activity, e.g. similar to that of compounds of formula I.

In another aspect the present invention provides a compound of formula I or of formula II in the form of a salt.

Such salts include preferably pharmaceutically acceptable salts, although pharmaceutically unacceptable salts are included, e.g. for preparation/isolation/purification purposes. A salt of a compound of the present invention includes an acid addition salt. Acid addition salts include salts of a compound of formula I or of formula II with an acid, e.g. hydrogen fumaric acid, fumaric acid, naphthalin-1,5-sulphonic acid, hydrochloric acid, deuterochloric acid; e.g. hydrochloric acid or deuterochloric acid, preferably hydrochloric acid. A compound of the present invention may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of pure isomers or mixtures thereof, e.g. optical isomers, diastereoisomers, cis/trans conformers. A compound of the present invention may e.g. contain asymmetric carbon atoms and may thus exist in the form of enantiomers or diastereoisomeres and mixtures thereof, e.g. racemates. Any asymmetric carbon atom, e.g. to which $R_6$ and X are attached, may be present in the (R)-, (S)- or (R,S) -configuration, preferably in the (R)- or (S)-configuration. For example the group bound via the group X to the piperidine ring in a compound of formula I or of formula II may be in the (R)- or in the (S)-configuration or in the form of mixtures thereof. E.g. the amine group of the amino acid residue, e.g. valyl or histidinyl residue, which is acylating the nitrogen atom of the piperidene ring may be in the (S)-configuration, in the (R)-configuration or in the form of mixtures therof. Isomeric mixtures may be separated as appropriate, e.g. according to a method as conventional, to obtain pure isomers. The present invention includes a compound of the present invention in any isomeric form and in any isomeric mixture. The present invention also includes tautomers of formula I or of formula II, where tautomers can exist. Preferably the configuration in the mutilin ring of a compound of the present invention is the same as in a naturally produced mutilin.

Isomeric mixtures may be separated as appropriate, e.g. according, e.g. analogously, to a method as conventional, to obtain pure isomers.

In another aspect the present invention provides a process for the production of a compound of formula I or of formula II comprising the steps A) for the production of a compound of formula I or of formula II wherein

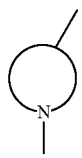

is piperidinyl, and the other residues are as defined above comprising the steps a) reacting a compound of formula

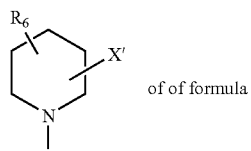

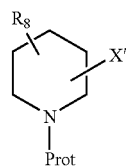

wherein Prot is a protecting group, e.g. BOC, X' is —SH or —NH-ALK, and $R_6$, $R_8$ and ALK are as defined above, with a 22-O-tosyl-pleuromutilin and tert.But-OK to obtain a compound of formula II, wherein $R_7$ is a protecting group, e.g. BOC, and the other residues are as defined above, b) deprotecting the nitrogen group of the piperidinyl ring in a compound obtained in step a), e.g. by use of etheric HCl, to obtain a compound of formula I, wherein $R_5$ is hydrogen and the other residues are as defined above, c) reacting a compound obtained in step b) with an amino-protected, e.g. BOC-protected, amino acid, e.g. valine or histidine, to obtain a compound of formula II, wherein $R_7$ is the residue of a protected amino acid, e.g. protected valine or histidine, preferably BOC-protected valine or histidine and the other residues are as defined above, d) deprotecting the amino group of the amino acid residue of a compound obtained in step c) to obtain a compound of formula I, wherein $R_5$ is a residue of an amino acid, e.g. valyl or histidinyl; e.g. in the form of a salt, such as a hydrochloride, e) optionally introducing deuterium into a compound of formula I obtained in step d) to obtain a compound of formula I, wherein $R_2$, $R_3$ and $R_4$ are deuterium, and $R_1$, $R'_1$ and $R_5$ are as defined above, B) for the production of a compound of formula I or of formula II wherein

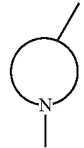

is tetrahydropyridinyl

B1) if the tetrahydropyridinyl is a 1,2,3,6-tetrahydropyridinyl, a) reacting a compound of formula

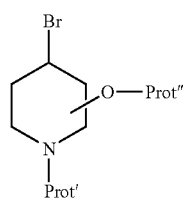   VIII wherein Prot' is either a protecting group or the residue of a protected amino acid, e.g. wherein the residue of an protected amino acid is as defined above, and Prot" is a protecting group, e.g. —CO—CH$_3$, in the presence of DBU to obtain a compound of formula

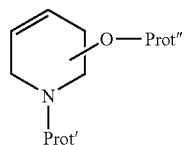   V wherein Prot' and Prot" are as defined above, b) removing the protecting group Prot" from a compound of formula V to obtain a compound of formula

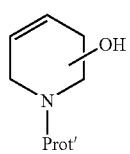   VI wherein Prot' is as defined above, c) reacting the hydroxy group in a compound of formula VI with mesylchloride and the mesylate obtained with thiapleuromutiline or HN-alkyl-pleuromutilin to obtain a compound of formula II, wherein

is a 1,2,3,6-tetrahydropyridinyl, and the other residues are as defined above, and d) removing the protecting Prot', if Prot' is a protecting group to obtain a compound of formula I wherein

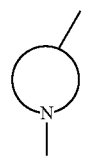

is a 1,2,3,6-tetrahydropyridinyl, R$_5$ is hydrogen and the other residues are as defined above; or removing the protecting group from the residue of the protected amino acid if Prot' is the residue of a protected amino acid, to obtain a compound of formula I wherein

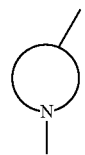

is a 1,2,3,6-tetrahydropyridinyl, R$_5$ is the residue of an amino acid and the other residues are as defined above;

B2) if the tetrahydropyridinyl is a 1,4,5,6-tetrahydropyridinyl a) reacting a compound of formula

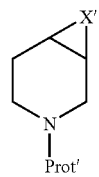   VII wherein X' and Prot' are as defined above, with 22-O-tosylpleuromutilin in the presence of n-butyl-lithium to obtain a compound of formula II, wherein

is a 1,4,5,6-tetrahydropyridinyl, R$_7$ is Prot', wherein Prot' is as defined above and the other residues are as defined above, and b) removing the protecting Prot' if Prot' is a protecting group to obtain a compound of formula I wherein

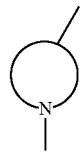

is a 1,4,5,6-tetrahydropyridinyl, $R_7$ is hydrogen and the other residues are as defined above; or removing the protecting group from the residue of the protected amino acid if Prot' is the residue of a protected amino acid, to obtain a compound of formula I wherein

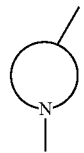

is a 1,4,5,6-tetrahydropyridinyl, $R_5$ is the residue of an amino acid and the other residues are as defined above.

In another preferred aspect of the present invention a compound of formula II, and, in consequence, e.g. according to step b) to f) of the present invention, a compound of formula I, wherein

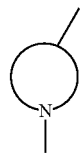

is piperidinyl, X is S and $R_6$ is hydrogen may be obtained by reaction of a compound of formula

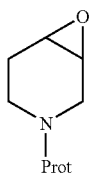

IV with thiapleuromultilin and $Al_2O_3$ to obtain a mixture of compounds of formula II, wherein $R_7$ is a protecting group, e.g. BOC, and wherein in one of the compounds of the mixture the hydroxy group is in position 3 and the sulphur group of the thiapleuromultilin is in position 4 of the piperidine ring, and in the other compound of the mixture the hydroxy group is in position 4 and the sulphur group of the thiapleuromutilin is in position 3 of the piperidine ring. That regioisomeric mixture may be separated to obtain pure compounds of formula II which pure compounds of formula II may be treated further according to steps b) to f) of the present invention to obtain pure compounds of formula I; or the regioisomeric mixture of compounds of formula II may be treated further according to steps b) to f) of the present invention to obtain a mixture of corresponding regioisomers of compounds of formula I which mixture may be separated to obtain pure compounds of formula I.

Separation of regioisomers may be carried out as appropriate, e.g. by chromatography.

If in step A)c) of the present invention the amino acid is used in the (R)-form, e.g.(R)-valine, (R)-histidine, a compound of formula I or II is obtained, wherein the amine group of the (protected) amino acid group attached to nitrogen atom of the piperidine ring is in the (R)-configuration; and if in step A)c) of the present invention the amino acid is used in the (S)-form, e.g.(S)-valine, (S)-histidine, a compound of formula I or II is obtained, wherein the amine group of the (protected) amino acid group attached to nitrogen atom of the piperidine ring is in the (S)-configuration.

Protecting groups in a production process include appropriate protecting groups, e.g. such as useful in organic chemistry, e.g. (pleuro)mutilin chemistry, e.g. protecting groups as conventional, such as BOC or —CO—$CH_3$.

Replacement of hydrogen atoms in a compound of formula I or of formula II, e.g. in the form of a salt, by deuterium atoms may be carried out as appropriate, e.g. according to a method as conventional, e.g. or according to a method described herein, e.g. by treatment of a compound of formula I or of formula II with deuterochloric acid (DCI) in an appropriate solvent (system) and isolation of a compound of formula I or of formula II, e.g. in the form of a salt, wherein hydrogen atoms, e.g. in the meaning of $R_2$, $R_3$ and $R_4$, are replaced by deuterium atoms. The production of a compound of formula I or of formula II, wherein $R_1$ and $R'_1$ is deuterium may be carried out as appropriate, e.g. according to a method as conventional, e.g. via treatment of a compound of formula

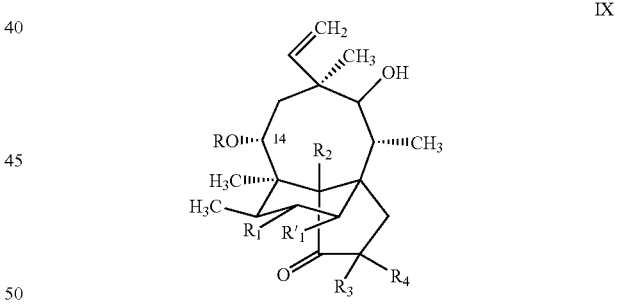

IX wherein the carbon atoms carrying $R_1$ and $R'_1$, which both are hydrogen, together form a double bond and wherein $R_2$, $R_3$ and $R_4$ are hydrogen, which is a known compound, with deuterium; to obtain a compound of formula IX, wherein $R_1$ and $R'_1$ are deuterium and $R_2$, $R_3$ and $R_4$ are hydrogen; and further reacting a compound of formula IX, wherein $R_1$ and $R'_1$ are deuterium and $R_2$, $R_3$ and $R_4$ are hydrogen as appropriate, e.g. according to a method as conventional, to obtain a compound of formula I or of formula II, wherein, $R_1$ and $R'_1$ are deuterium and $R_2$, $R_3$ and $R_4$ are hydrogen. R is a residue which is chemically not affected by deuterium addition, e.g. —CO—$CH_2OH$.

Intermediates in the preparation of compounds of formula I includes compounds of formula III, III', IV, V, VI, VII, VIII or IX, and are known or may be obtained according to a method as conventional. Any compound described herein may be produced according, e.g. analogously, to a process as conventional, or as described herein.

The compounds of the present invention, e.g. including a compound of formula I exhibit pharmacological activity and are therefore useful as pharmaceuticals. The compounds of formula II may be useful intermediates in the preparation of compounds of formula I, which, however, may also exhibit pharmacological activity, e.g. similar to that of compounds of formula I.

For example, the active compounds of the present invention (e.g. and compounds of formula II) show antimicrobial, e.g. antibacterial, activity against gram positive bacterias and gram negative bacterias, e.g. gram negative bacterias such as *Escherichia coli*, and against gram positive bacteria, such as *Staphylococcus aureus* and in addition *Streptococcus pyogenes* and *Streptococcus pneumoniae*, Mycoplasms, *Chlamydia, Helicobacter* spec. and obligatory anaerobes, e.g. *Bacteroides fragilis*, in vitro in the Agar Dilution Test or Microdilution Test according to National Commitee for Clinical Laboratory Standards (NCCLS) 1997, Document M7-A4 Vol. 17, No. 2: "Methods for dilution Antimicrobial Susceptibility Tests for Bacteria that Grow Aerobically—Fourth Edition, Approved Standard" and e.g. in vivo in systemic infections in mice. The active compounds of the invention show an surprising overall activity spectrum.

In another aspect the present invention provides a compound of formula I, e.g. or of formula II, for use as a pharmaceutical, preferably as an antimicrobial, such as an antibiotic.

For pharmaceutical use a compound of the present invention includes one or more, preferably one, compounds of the present invention, e.g. a combination of two or more compounds of the present invention.

In a further aspect the present invention provides the use of a compound of the present invention, e.g. a compound of formula I e.g. or of formula II, for the manufacture of a medicament, e.g. a pharmaceutical composition, for the treatment of a microbial disease, for example of a disease mediated by bacteria, e.g. bacteria selected from *Staphylococcus aureus, Streptococcus pyogenes, Streptococcus pneumoniae,* Mycoplasms, *Chlamydia* e.g. *C. trachomatis* and *C. pneumoniae* and obligatory anaerobes, e.g. including penicillin or multidrug-resistant strains, e.g. of *Streptococcus pneumoniae;* e.g. including vancomycin-resistant strains, e.g. of *Enterococcus faecium;* e.g. and including methicillin-resistant strains, e.g. of *Staphylococcus aureus* and *Helicobacter* spec., e.g. *H. pylori*.

In another aspect the present invention provides a compound of the present invention or a pharmaceutical composition of the present invention for use in the preparation of a medicament for the treatment of microbial diseases.

In a further aspect the present invention provides a method of treatment of microbial diseases which comprises administering to a subject in need of such treatment an effective amount of a compound of the present invention, e.g. a compound of formula I, e.g. or of formula II, e.g. in the form of a pharmaceutical composition.

Treatment includes treatment and prophylaxis.

For antimicrobial treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.1 to 3 g, e.g. 0.00125 g/kg to 0.0375 g/kg, of a compound of the present invention conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutanous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as clarithromycin and azithromycin.

The compounds of the present invention may be administered in the form of a pharmaceutically acceptable salt, e.g. an acid addition salt or metal salt; or in free form; optionally in the form of a solvate. The compounds of the present invention in the form of a salt exhibit the same order of activity as the compounds of the present invention in free form; optionally in the form of a solvate.

A compound of the present invention may be used for pharmaceutical treatment according to the present invention alone or in combination with one or more other pharmaceutically active agents. Such other pharmaceutically active agents include e.g. other antibiotics. Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention, e.g. a compound of formula I or, e.g. of formula II, in free form or in the form of a pharmaceutically acceptable salt; e.g. and/or in the form of a solvate; in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes.

Unit dosage form may contain, for example, from about 0.5 mg to about 1500 mg, such as 1 mg to about 500 mg, e.g. 1 mg to about 100 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of formula I, e.g. or of formula II, for use as a veterinary agent.

In a further aspect the present invention provides a compound of formula I, e.g. or of formula II, for the preparation of a veterinary composition which is useful as a veterinary agent.

In another aspect the present invention provides a veterinary method for the prophylaxis and in the treatment of microbial, e.g. bacterial diseases which comprises administering to a subject in need of such treatment an effective amount of a compound of formula I, e.g. or of formula II, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 3 weeks. Preferred doses in drinking water are from 0.0125 to 0.05 g/ml, particularly 0.0125 to 0.025 g/ml; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

In another aspect the present invention provides a compound of formula

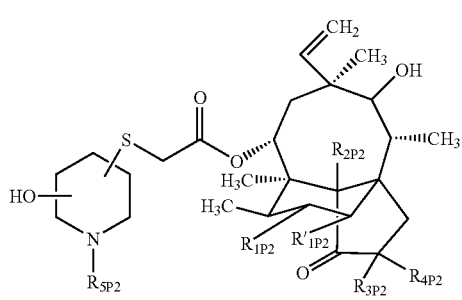

I wherein
$R_{1P2}$ and $R'_{1P2}$ are hydrogen or deuterium,
$R_{2P2}$, $R_{3P2}$ and $R_{4P2}$ are hydrogen or deuterium, and
$R_{5P2}$ is hydrogen or a residue of an amino acid.

In another aspect the present invention provides a compound of formula

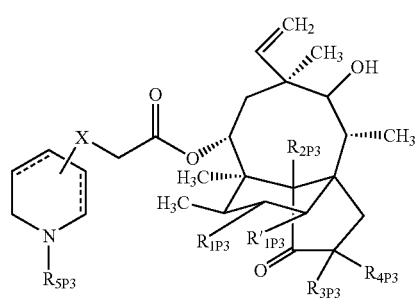

I wherein
$R_{1P3}$ and $R'_{1P3}$ are hydrogen or deuterium,
$R_{2P3}$, $R_{3P3}$ and $R_{4P3}$ are hydrogen or deuterium,
$R_{5P3}$ is hydrogen or a residue of an amino acid,
X is S or N-ALK, one of the dotted lines is a bond and the other is no bond; or one of the dotted lines is a group —OAc attached to the piperidine ring in position 2, 3, 4, 5 or 6, and the other dotted line is no bond,
ALK is $(C_{1-4})$alkyl, e.g. methyl, and
Ac is hydrogen or $(C_{2-12})$acyl, e.g. a group —CO—CH$_3$, with the proviso that if X is S and one of the dotted lines is a group OAc and the other dotted line is no bond, then Ac is other than hydrogen.

In the following examples all temperatures are in degrees Celsius (° C.) and are uncorrected.

The following abbreviations are used:
BOC tert.butyloxycarbonyl
DBU 1,8-diazabicyclo[5.4.0]undec-7-en(1,5-5)
Diast. mixtures of diastereoisomers
EDC N-(3-dimethylaminopropyl)-N-ethylcarbodiimide
EE ethyl acetate
EtOH ethanol
EX Example
HOBT hydroxybenztriazole
RT room temperature
THF tetrahydrofurane
TBAF tetrabutylammoniumfluoride
tert.But-OK tert.butoxide potassium
$^1$H-NMR data is determined in CDCl$_3$ if not otherwise indicated.

Valyl and N-BOC-valyl are groups of formula

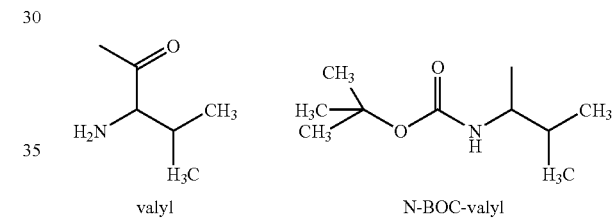

valyl      N-BOC-valyl

Histidinyl and N-BOC-histidinyl are groups of formula

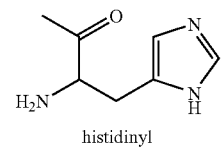

histidinyl

N-BOC-histidinyl

N-BOC-3,4-Epoxy-piperidine is a compound of formula

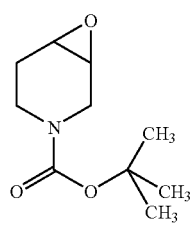

Pleuromutilin is a compound of formula

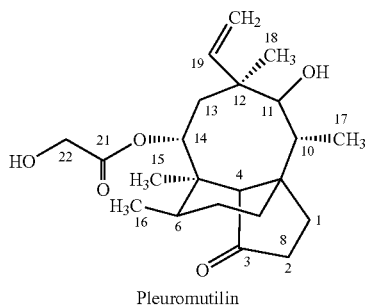

Pleuromutilin

A group of formula

is a group of formula Pleuromutilin, missing the group —CO—CH₂OH.

Thiapleuromutilin is a compound of formula

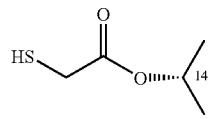

22-O-Tosylpleuromutilin is a compound of formula

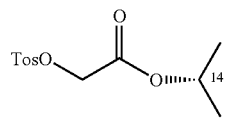

wherein Tos is a tosyl group.
HN-alkyl-pleuromutilin is a compound of formula

EXAMPLE 1

14-O—[N-BOC-4-Hydroxy-piperidin-3-yl]-sulfanylacetylmutilin and 14-O—[N-BOC-3-hydroxy-piperidin-4-yl]-sulfanylacetylmutilin 40 g of (neutrally) activated Al₂O₃, moistened with THF, are treated with a solution of 1.576 g of thiapleuromutiline in 5 ml of THF and to the mixture obtained 0.398 g of N-BOC-3,4-epoxy-piperidine, dissolved in 3 ml of THF, are added. From the mixture obtained Al₂O₃ is filtered off, from the filtrate obtained solvent is evaporated off and the evaporation residue comprising a mixture of 14-O—[N-BOC-4-hydroxy-piperidin-3-yl]-sulfanylacetylmutilin and 14-O—[N-BOC-3-hydroxy-piperidin-4-yl]-sulfanylacetylmutilin is subjected to chromatography.
14-O—[N-BOC-3-Hydroxy-piperidin-4-yl]-sulfanylacetylmutilin and
14-O—[N-BOC-4-Hydroxy-piperidin-3-yl]-sulfanylacetylmutilin are obtained.

14-O—[N-BOC-3-hydroxy-piperidin-4-yl]-sulfanylacetylmutilin is also obtained by reacting 0.466 g of N-BOC-3-hydroxy-4-mercaptopiperidine in 10 ml of THF with 0.224 g of tert.But-OK in 20 ml of THF, adding to the mixture obtained of a solution of 1.064 g of 22-O -tosylpleuromutilin in 5 ml THF, dropwise adding to the mixture obtained 1 ml of 2-butanone, stirring at RT and subjecting to chromatographic purification.

EXAMPLE 2

14-O-[4-Hydroxy-N—(N-BOC-valyl-piperidin-3-yl]-sulfanylacetylmutilin 1.5 mmol of 14-O-[4-hydroxy-piperidin-3-yl]-sulfanylacetylmutilin dissolved in 5 ml of CH₂Cl₂ are treated with 1.5 mmol of HOBT, 1 mmol of (R)-BOC-valin and 1.5 mmol of EDC and stirred at RT. From the mixture obtained solvent is evaporated, the evaporation residue obtained is mixed with EE and the mixture obtained is extracted with 0.1 N HCl and saturated aqueous NaHCO₃ solution. The organic phase obtained is dried and solvent is evaporated. 14-O-[4-Hydroxy-N—(N-BOC-(R)-valyl-piperidin-3-yl-sulfanylacetylmutilin is obtained.

EXAMPLE 3

14-O-[4-Hydroxy-N—(R)-valyl)-piperidin-3-yl]-sulfanylacetylmutilin 1 mmol of 14-O-[4-hydroxy-N—(N-BOC-(R)-valyl-piperidin-3-yl-sulfanylacetylmutilin in 5 to 8 ml of CH₂Cl₂ is treated with 1 to 2 ml of etheric HCl, the mixture obtained is stirred at RT and 14-O-[4-Hydroxy-N—(R)-valyl)-piperidin-3-yl]-sulfanylacetylmutilin in the form of a hydrochloride precipitates and is isolated by filtration.

EXAMPLE 4

14-O—[N—(N-BOC-valyl)-1,2,3,6-tetrahydropyridin-3-yl]-sulfanylacetylmutilin a) 3-Mesyloxy-N—(N-BOC-(R)-valyl)-1,2,3,6-tetrahydropyridine
0.894 g of N—(N-BOC-(R)-valyl)-1,2,3,6-tetrahydropyridin-3-ol dissolved in 10 ml of CH₂Cl₂ are treated with 0.844 g of 4-dimethylaminopyridine and 0.31 g of methanesulfonic acid chlorid (mesylchloride) and stirred for ca. 24 hours, the mixture obtained is treated with 0.1 N HCl and CH₂Cl₂, the organic phase obtained is washed with H₂O and aqueous NaHCO₃-solution, the solvent is evaporated and the evaporation residue is dried. 3-Mesyloxy-N—(N-BOC-(R)-valyl)-1,2,3,6-tetrahydropyridine is obtained. ¹H-NMR (CDCl₃): 6.1-5.85(m,2H,H$_{IV}$,H$_V$), 4.5(m,1H,NHC$\underline{H}$CO), 3.7(s,3H, CH₃SO₂), 1.2-0.9(m,6H,(C$\underline{H}_3$)₂.
b) 14-O—[N—(N-BOC-(R)-valyl)-1,2,3,6-tetrahydropyridin-3-yl]-sulfanylacetylmutilin
0.235 tert.But-OK dissolved in 5 ml of THF are treated with thiapleuromutilin in 10 ml of THF and to the mixture obtained 0.789 g of 3-mesyloxy-N—(N-BOC-(R)-valyl)-1,2,3,6-tetrahydropyridine in 10 ml of THF are added dropwise. The mixture obtained is heated to 90° and stirred at RT. The mixture obtained is treated with diluted aqueous HCl, the organic phase obtained is washed and solvent is evaporated. 14-O—[N—(N-BOC-(R)-valyl)-1,2,3,6-tetrahydropyridin-3-yl]-sulfanylacetylmutilin is obtained.

EXAMPLE 5

14-O—[N-BOC-1,4,5,6-tetrahydropyridin-4-yl]-sulfanylacetylmutilin 2.72 ml of diisopropylamine in 40 ml of THF are treated with 12 ml n-butyl-lithium (1.6 M solution in hexane) at −40° and the mixture obtained is stirred, warmed to −10° and a solution of 3.44 g of N-BOC-1,2,5,6-tetrahydropyridine in 20 ml of THF is added dropwise. To the mixture obtained a solution of 22-O-tosylpleuromutilin in 10 ml of THF and 1 ml of 2-butanone are added and the mixture obtained is stirred at RT. The mixture obtained comprising a mixture of 14-O—[N-BOC-1,4,5,6-tetrahydropyridin-4(R*)-yl]-sulfanylacetyl-mutilin (COMPOUND A) and 14-O—[N-BOC-1,4,5,6-tetrahydropyridin4(S*)-yl]-sulfanylacetylmutilin (COMPOUND B) is subjected to chromatography and pure COMPOUND A and pure COMPOUND B are obtained.

EXAMPLE 6

14-O—[N—(N-BOC-valyl)-1,4,5,6-tetrahydropyridin-4-yl]-sulfanylacetylmutilin 4.53 ml of diisopropylamine in 30 ml of THF are treated with n-butyl-lithium (1.6 M solution in n-hexane) at −40° C. The mixture obtained is stirred, warmed up to −10° and a solution of 5.02 g of 3,4-epithio-N(N-BOC-(R)-valyl)-piperidine in 30 ml of THF is added. The mixture obtained is stirred for ca. 3 hours at −10°, a solution of 22-O-tosylpleuromutilin in 20 ml of THF and 5 ml of 2-butanone are added and the mixture obtained is stirred at RT. The mixture obtained is subjected to extractive work up and chromatography. 14-O—[N—(N-BOC-(R)-valyl)-1,4,5,6-tetrahydropyridin-4-yl]-sulfanylacetylmutilin is obtained.

Analogously as described in the previous examples, but using appropriate starting materials, compounds of formula

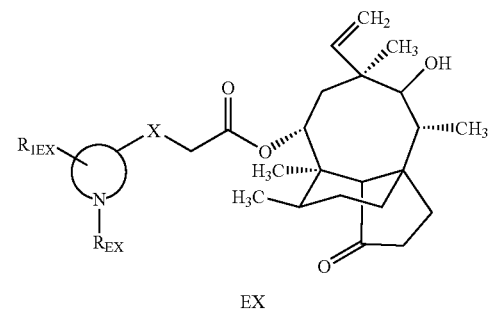

EX wherein X, $R_{EX}$ and $R_{1EX}$ are as set out in TABLE 1 below. If a compound is obtained in salt form, this is indicated in column 6. $^1$H-NMR of a compound obtained (optionally in salt form) is also set out in TABLE 1.

TABLE 1

| EX | X | $R_{EX}$ | $R_{1EX}$ |  | Salt form (if any) $^1$H-NMR-data |
|---|---|---|---|---|---|
| 1a | S | BOC | 4-hydroxy | piperidin-3-yl | Diast.: 4.28(m, 1H, $H_{II}$), 4.15–4.0 (b, 1H, $H_{VI}$), 3.6–3.32(b, 3H, $H_{11}$), (1.45(s, 9H, $(CH_3)_3$) |
| 1b | S | BOC | 3-hydroxy | piperidin-4-yl | Diast.: 4.3(b, 1H, $H_{II}$), 4.05(m, 1H, $H_{VI}$), 3.45(m, 1H, $H_{IV}$), 3.28 (b, 2H, $H_{22}$), 2.8–2.6(m, 2H, $H_{II'}$, $H_{VI}$), 2.55(m, 1H, $H_{III}$), 1.45 (s, 9H, $(CH_3)_3$) |
| 2 | S | N-BOC-(R)-valyl | 4-hydroxy | piperidin-3-yl | Rotameres/Diaster.: 5.75(m, 1H, NHCO), 4.75, 4.2, 3.95(3xm, 1H, $H_{II}$), 4.45, 4.35(2xm, 1H, NHCO), 3.55(m, 1H, $H_{IV}$), 3.35(m, 1H, $H_{11}$), 3.3(s, 2H, $H_{22}$), 2.55(m, 1H, $H_{III}$), 1.45(b, 12H, $(CH_3)_3$, $(CH_3)_{15}$), 0.95, 0.7(2xm, 6H, $CH(CH_3)_2$ |
| 3 | S | (R)-valyl | 4-hydroxy | piperidin-3-yl | Hydrochloride Diast.: 8.35(b, 3H, $NH_3^+$), 4.5(m, 2H, $H_{II}$, NHCHCO), 3.45–3.3(m, 3H, $H_{11}$, $H_{22}$), 2.7, 2.55(2xm, 1H, $H_{III}$), 3.6(m, 1H, $H_{IV}$), 1.1 (m, 6H, $CH(CH_3)_2$ |
| 4 | S | N-BOC-(R)-valyl | H | 1,2,3,6-tetrahydro-pyridin-3-yl | 5.95–5.75(m, 2H, $H_{IV}$, $H_V$), 4.45(m, 1H, NHCHCO), 1.45(s, 9H, $(CH_3)_3$), 0.9(m, 9H, $(CH_3)_{17}$, $(CH_3)_2$) |
| 5a | S | BOC | H | 1,4,5,6-tetrahydro-pyridin-4(R*)-yl | Rotameres: 6.9, 6.7, 4.85, 4.75 (4xm, 2H, $H_{II}$, $H_{III}$), 3.8(m, 1H, $H_{VI}$), 3.45(m, 1H, $H_V$), 3.35–3.15(m, 3H, $H_{11}$, $H_{22}$), 2.9(m, 1H, $H_{IV}$), 1.4(b, 9H, $(CH_3)_3$) |
| 5a | S | BOC | H | 1,4,5,6-tetrahydro-pyridin-4(S*)-yl | $d_6$-DMSO, 350 K: Rotameres: 6.8(d, 1H, $H_{II}$, J = 8.3Hz), 4.82(dt, 1H, $H_{III}$, J = 8.3Hz, J = 4.9Hz), 4.15 (m, 1H, $H_{VI}$), 3.7(m, 1H, $H_{IV}$), 3.55 (m, 1H, $H_{VI}$), 3.45, 3.39(2xm, 2H, |

TABLE 1-continued

| EX | X | $R_{EX}$ | $R_{1EX}$ | ⟨N⟩ ring | Salt form (if any) ¹H-NMR-data |
|---|---|---|---|---|---|
| | | | | | $H_{V}$), 2xAB-System: $v_A = 3.32$, $v_A = 3.3$, $v_B = 3.23$, $v_B$ 3.21 (2H, $H_{22}$, J = 14.8Hz, J = 14.9Hz), 1.4 (s, 9H, (CH$_3$)$_3$) |
| 6 | S | N-BOC-(R)-valyl | H | 1,4,5,6-tetrahydro-pyridin-4-yl | Rotameres/Diast.: 7.25, 6.8, 5.15, 5.05 (4xm, 2H, $H_{II}$, $H_{III}$), 5.3(d, 1H, NHCHCO, J = 4.6Hz), 4.58(m, 1H, $H_{IV}$), 4.25, 4.05, 3.98(3xd, 1H, NHCHCO), 3.65 (m, 1H, $H_{vi}$), 3.5 (m, 1H, $H_{v}$), AB-system: $v_A = 3.25$, $v_B = 3.15$(2H, $H_{22}$, J = 15Hz), 1.48(b, 9H, (CH$_3$)$_3$), 1.0, 0.9(2xd, 6H, CH(CH$_3$)$_2$) |
| 7 | S | (R)-valyl | 3-hydroxy | piperidin-4-yl | Hydrochloride d$_6$-DMSO, 350 K: Diast. : 8.05(b, 3H, NH$_3^+$), 4.25–4.1(m, 3H, $H_{II}$, $H_{VI}$, NHCHCO), 3.75(m, 1H, $H_{III}$), 3.45–3.32(m, 3H, $H_{11}$, $H_{22}$), 2.89(m, 1H, $H_{IV}$), 0.98, 0.92(2xd, 6H, CH(CH$_3$)$_2$, J = 6 Hz) |
| 8 | S | (R)-histidinyl | 3-hydroxy | piperidin-4-yl | Dihydrochloride d$_6$-DMSO, 350K: Diast.: 8.88, 7.45 (2xs, 2H, aromat.H$_{imidazol}$), 4.75 (m, 1H, NHCHCO, AB-System: $v_A = 3.43$, $v_B = 3.38$ (2H, $H_{22}$, J = 15Hz), 3.48 (d, 1H, $H_{11}$, J = 6Hz), AB-System: $v_A = 3.23$, $v_B = 3.15$(2H, NHCHCH$_2$, J = 8.3Hz, J = 15.6Hz) |
| 9 | NCH$_3$ | (R)-valyl | 3-hydroxy | piperidin-4-yl | Dihydrochloride d$_6$-DMSO, 350 K: Diast.: 8.35, 8.15(2xb, 4H, CH$_3$NH$^+$, NH$_3^+$), 4.21 (b, 1H, NHCHCO), 3.35(m, 2H, $H_{22}$), 2.86, 2.83(2xb, 3H, CH$_3$NH$^+$), 0.94(d, 6H, CH(CH$_3$)$_2$, J = 6Hz) |
| 10 | NCH$_3$ | (R)-valyl | 4-hydroxy | piperidin-3-yl | Dihydrochloride d$_6$-DMSO: Diast.: 8.3, 8.2(2xb, 4H, CH$_3$NH$^+$, NH$_3^+$), 4.1(m, 1H, NHCHCO), 3.45(b, 2H, $H_{22}$), 2.95, 2.9(2xs, 3H, CH$_3$NH$^+$), 0.95(m, 6H, CH(CH$_3$)$_2$) |
| 11a | S | (R)-valyl | H | 1,2,3,6-tetrahydro-pyridin-3(R*)-yl | Rotameres: 5.95–5.75(m, 3H, $H_{14}$, $H_{IV}$, $H_{V}$), 2xAB-system: $v_A = 4.22$, $v_A = 4.09$, $v_B = 3.9$, $v_B = 4.0$(2H, $H_{vi}$, J = 19.2Hz), AB-system: $v_A = 4.2$, $v_B = 3.77$(2H, $H_{III}$, J = 17.7Hz), 3.68–3.6 (m, 1H, $H_{III}$), 3.52(m, 1H, NHCHCO), 3.2(m, 2H, $H_{22}$), $H_{22}$, $J_{22,sH} = 8.2$Hz, $J_{AB} = 15.1$Hz, $J_{AX} = 8.2$Hz) |
| 11b | S | (R)-valyl | H | 1,2,3,6-tetrahydro-pyridin-3(S*)-yl | Rotameres: 5.98–5.78(m, 2H, $H_{IV}$, $H_{V}$), 5.78(d, 1H, $H_{14}$, J = 8.4Hz), 3xAB-system: $v_A = 4.7$, $v_A = 4.61$, $v_A = 4.5$, $v_B = 3.8$, $v_B = 3.7$, $v_B$ 3.42 (2H, $H_{vi}$, J$_1$ = 19.5Hz, J$_2$ = 18.9Hz, J$_3$ = 14.4Hz), 3xAB-system: $v_A = 4.35$, $v_A = 4.1$, $v_A = 3.88$, $v_B = 3.98$, $v_B = 3.7$, $v_B = 3.72$, $v_B = 3.46$(2H, $H_{II}$, J$_1$ = 13.7Hz, J$_2$ = 13.7Hz, J$_3$ = 13.9Hz), 3.65(m, 1H, $H_{III}$), 3.58(m, 1H, NHCHCO) |
| 12 | S | (R)-valyl | 4-acetoxy | piperidin-3-yl | d$_6$-DMSO: Diast.: 8.1(b, 3H, NH$_3^+$), 4.52(m, 1H$H_{IV}$), 4.32, 4.28 (2xm, 1H, NHCHO), 3.5–3.35(m, 4H, $H_{11}$, $H_{22}$, $H_{VI}$), 2.93, 2.88(2xm, 1H, $H_{II}$), 2.03, 2.02, 2.00(3xs, 3H, OCOCH$_3$), 0.98, 0.88(2xm, 6H, CH(CH$_3$)$_2$) |
| 13 | S | N-BOC-(R)-valyl | 3-hydroxy | piperidin-4-yl | Hydrochloride Rotameres/Diast.: 6.8, 6.68(2m, 1H, NHCHCO), 5.32(m, 1H, OH), 4.2(m, 1H, NHCHCO), 3.85(m, 1H, $H_{VI}$), 3.5–3.3(m, 3H, $H_{11}$,$H_{22}$), 3.15 |

TABLE 1-continued

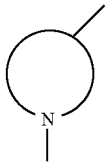

| EX | X | $R_{EX}$ | $R_{1EX}$ | Salt form (if any) ¹H-NMR-data |
|---|---|---|---|---|
| 14 | S | N-BOC-(R)-histidinyl | 3-hydroxy piperidin-4-yl | (m, 1H, $H_{III}$), 2.8(m, 1H, $H_{IV}$), 1.35(s, 12H, $(CH_3)_3$, $(CH_3)_{15}$), 0.8(m, 9H, $CH(CH_3)_2$), $(CH_3)_{17}$) $d_6$-DMSO, 350K: Diast.: 8.21, 8.02 (2xs, 2H, aromat.$H_{imidazol}$), 7.18(d, 1H, NHCHCO, J = 3.1 Hz), 6.55 (b, 1H, OH), 4.65(m, 1H, $H_{VI}$), H4, 15 (m, 1H, NHCHCO), 3.5–3.1(m, 5H, NHCHCH₂, $H_{11}$, $H_{22}$), 2.8(m, 1H, $H_{IV}$), 1.55, 1.35(2xs, 18H, 2x$(CH_3)_3$) |
| 15 | NCH₃ | BOC | 4-hydroxy piperidin-3-yl | Diast.: 4.2–4.0(b, 2H, $H_{II}$, $H_{VI}$), 3.5 (m, 1H, $H_{IV}$), 3.4–3.2(m, 3H, $H_{11}$, $H_{22}$), 2.65, 2.5,(2xm, 2H, $H_{II}$, $H_{VI}$), 2.42 (s, 3H, NCH₃), 1.45(s, 12H, $(CH_3)_3(CH_3)_{15}$) |
| 16 | NCH₃ | BOC | 3-hydroxy piperidin-4-yl | Diast.: 4.4, 4.2(2xm, 2H, $H_{II}$, $H_{VI}$), 3.4–3.12(m, 4H, $H_{11}$, $H_{22}$, $H_{III}$), 2.58, 2.49(2xm, 2H, $H_{II}$, $H_{VI}$), 2.38(s, 3H, NCH₃), 1.45(b, 12H, $(CH_3)_3(CH_3)_{15}$) |
| 17 | S | N-BOC-(R)-valyl | 4-acetoxy piperidin-3-yl | $d_6$-DMSO: Diast.: 8.1 (b, 3H, $NH_3^+$), 4.52(m, 1H, $H_{IV}$), 4.32, 4.28 (2xm, 1H, NHCHCO), 3.5–3.35(m, 4H, $H_{11}$, $H_{22}$, $H_{VI}$), 2.93, 2.88(2xm, 1H, $H_{III}$), 2.03, 2.02, 2.01 (3s, 3H, OCOCH₃).0.98, 0.88(2xm, 6H, $CH(CH_3)_2$) |
| 18 | S | N-BOC-(R)-valyl | 3-acetoxy piperidin-4-yl | $d_6$-DMSO: Diast.: 8.05(b, 3H, $NH_3^+$), 4.62(m, 1H, NHCHCO), 4.52(m, 1H, $H_{III}$), 4.25, 4.18(2xm, 1H, $H_{VI}$), AB-system: $v_A$ = 3.95, $v_B$ = 3.65(2H, $H_{II}$, J = 2.8Hz, J = 12.6Hz), 3.4(m, 3H, $H_{11}$, $H_{22}$), 3.12(m, 1H,) $H_{IV}$), 0.98, 0.88(2xm, 6H, $CH(CH_3)_2$ |
| 19 | NCH₃ | N-BOC-(R)-valyl | 4-hydroxy piperidin-3-yl | Diast.: 4.2–4.0(b, 2H, $H_{II}$, $H_{VI}$), 3.5 (m, 1H, $H_{IV}$), 3.4–3.2(m, 3H, $H_{11}$, $H_{22}$), 2.65, 2.5(2xm, 2H, $H_{II}$, $H_{VI}$), 2.42(s, 3H, NCH₃), 1.45(s, 12H, $(CH_3)_3(CH_3)_{15}$)) |
| 20 | NCH₃ | N-BOC- | 3-hydroxy piperidin-4-yl | Diast.: 4.4, 4.2(2xm, 2H, $H_{II}$, $H_{VI}$), 3.4–3.12(m, 4H, $H_{11}$, $H_{22}$, $H_{III}$), 2.58–2.49(2xm, 2H, $H_{II}$, $H_{VI}$), 2.38 (s, 3H, NCH₃), 1.45(b, 12H, $(CH_3)_3(CH_3)_{15}$) |

Production of Starting Material

Example A

Thiapleuromutilin

Thiapleuromutilin in the Form of the Isothiuronium Salt

A mixture of 106.4 g of 22-O-tosylpleuromutilin, 15.2 g of thiourea and 250 ml of acetone is refluxed for ca. 1.5 hours, cooled and from the mixture obtained solvent is evaporated and the evaporation residue is dried in vacuo. Thiapleuromutilin in the form of an isothiuronium salt is obtained.
¹H-NMR: 9.82,8.42(2xb, 2H,NH₂),7.78, 7.2(2xd,4H,arom. $H_{Tosyl}$,J=15.8 Hz)

a) Thiapleuromutilin 24.4 g of thiapleuromutilin in the form of an isothiuronium salt, dissolved in 40 ml absolute EtOH, is diluted with 70 ml of H₂O and warmed to 90°. The mixture obtained is treated with 7.6 g of sodium disulfite in 35 ml of H₂O and to the mixture obtained 200 ml of CH₂Cl₂ are added. The mixture obtained is heated to 90° for ca. 1.5 hours and cooled. Two phases are formed and are separated, the organic phase obtained is washed, dried, solvent is evaporated and the evaporation residue is filtered through silicagel. Thiapleuromutilin is obtained.

¹H-NMR: 6.48(dd,1H,$H_{19}$,$J_{19,20cis}$=11 Hz,$J_{19,20trans}$=16.5 Hz), 5.75(d,1H,$H_{14}$,$J_{13,14}$=8.5 Hz), 5.38(dd,1H,$H_{20}$,$J_{20,20}$= 1.5 Hz), 5.2(dd,1H,$H_{20trans}$), 3.38(dd,1H,$H_{11}$,$J_{11,OH}$=10.4 Hz, $J_{11,10}$=6.6 Hz), ABX-System: $v_A$=3.21, $v_B$=3.18,$v_X$=1.9 ($H_{22}$,$J_{22,sH}$=8.2 Hz,$J_{AB}$=15.1 Hz,$J_{AX}$=8.2 Hz), 2.35(quint.1H, $H_{10}$,$J_{10,17}$=8.2 Hz), 2.28, 2.2(2H, $H_{H2\alpha,2\beta}$,$J_{2\alpha,2\beta}$=15.5 Hz,$J_{2\alpha,1\alpha}$=$J_{2\alpha,1\beta}$=5.5 Hz), 2.19(dd,1H,$H_{13}$,$J_{13,13}$=16 Hz, $J_{13,14}$=8.5 Hz), 2.12(b,1H,$H_4$), 1.9(t,1H,SH,$J_{22,sH}$=8.2 Hz), 1.79, 176(2xq,1H,$H_{8equ}$.,$J_{7,8equ}$=3.01 Hz,$J_{8,8}$=14.5 Hz), 1.67 (m,2H,$H_1$,$H_6$), 1.57, 1.53(2xm,1H, $H_{7ax}$), 1.45(s,3H, $(CH_3)_{15}$), 1.39, 1.36(2xq,1H,$H_{7q}$,$J_{7,7}$=7.23 Hz), 1.33(d,1H, $H_{13}$), 1.18(s,3H, $(CH_3)_{18}$), 1.12(dd,1H,$H_{8ax}$,$J_{7,8ax}$=1.14 Hz), 0.89(d,3H,$(CH_3)_{17}$,$J_{10,17}$=6.54 Hz), 0.74(d,3H, $(CH_3)_{16}$, $J_{6,16}$=6.5 Hz). ¹H-NMR ($d_6$-DMSO): 2.85(s,1H,SH).

EXAMPLE B

N-BOC-3,4-Epoxy-piperidine a) N-BOC-1,2,5,6-tetrahydropyridine

To 1.66 g of 1,2,5,6-tetrahydropyridine in 25 ml of $CH_2Cl_2$, 2.02 g of N-methylmorpholine are added, the mixture obtained is treated with a solution of 4.36 g $(BOC)_2O$ in 30 ml of $CH_2Cl_2$ and the mixture obtained is stirred for ca. 36 hours at RT. N-BOC-1,2,5,6-tetrahydropyridine is obtained. $^1$H-NMR: 5.82(m,1H,$H_{IV}$), 5.64(m,1H,$H_{III}$), 3.86(b,2H,$H_{II}$), 3.47(t,2H,$H_{VI}$), 2.12(b,1H,$H_V$), 1.46(m,9H,$(CH_3)_3$).

b) N-BOC-3,4-Epoxy-piperidine

To a solution of 3.29 g of N-BOC-1,2,5,6-tetrahydropyridine in 25 ml of $CH_2Cl_2$, a suspension of 6.2 g of chloroperbenzoic acid in 50 ml of $CH_2Cl_2$ are added and the mixture obtained is stirred for ca. 12 hours at RT. The mixture obtained is extracted with saturated aqueous $NaHCO_3$-solution and 0.5 m aqueous $Na_2S_5O_3$-solution and the organic phase obtained is washed, dried and the solvent is evaporated. N-BOC-3,4-epoxy-piperidine is obtained.

$^1$H-NMR: 3.9, 3.65, 3.45, 3.1(4xm,4H,$H_{II}$,$H_{VI}$), 3.28, 3.2 (2xm,2H,$H_{III}$,$H_V$), 2.05, 1.9(2xm,2H,$H_V$), 1.45(s,9H, $(CH_3)_3$).

EXAMPLE C

N—(N-BOC-(R)-valyl)-1,2,3,6-tetrahydropyridin-3-ol a) N—(N-BOC-valyl-1,2,5,6-tetrahydropyridine 1.245 g of tetrahydropyridine in 50 ml of $CH_2Cl_2$ are treated with 1.5 mmol per mmol of tetrahydropyridine of HOBT, 2.17 g of N-BOC-(R)-valin and 1.5 mmol per mmol of tetrahydropyridine of EDC and the mixture obtained is stirred at RT. From the mixture obtained solvent is evaporated, the evaporation residue obtained is mixed with EE and the mixture obtained is extracted with 0.1N HCl and saturated aqueous $NaHCO_3$ solution. The organic phase obtained is dried and solvent is evaporated. N—(N-BOC-(R)-valyl-1,2,5,6-tetrahydropyridine is obtained.

b) 3.4-Epoxy-N—(N-BOC-valyl-1,2,5,6-tetrahydropyridine

To a solution of 2.82 g of N—(N-BOC-(R)-valyl-1,2,5,6-tetrahydropyridine in 75 ml of $CH_2Cl_2$, 3.44 g of m-chloroperbenzoic acid in 50 ml of $CH_2Cl_2$ are slowly added and the mixture obtained is stirred overnight. The mixture obtained is extracted with aqueous $NaHCO_3$-solution and with 0.5 m aqueous $Na_2S_2O_3$-solution, the phases obtained are separated and from the organic phase solvent is evaporated in vacuo. 3,4-Epoxy-N—(N-BOC-(R)-valyl-1,2,5,6-tetrahydropyridine is obtained. $^1$H-NMR: Rotameres: 5.3(m,1H, N HCHCO), 4.4(m,1H, NHCHCO), 4.3, 4.1, 4.0 (3dd,1H,$H_{III}$, J=15.6 Hz), 3.88, 3.78, 3.65(3xd,1H,$H_{IV}$,J=15.6 Hz), 3.6, 3.45, 3.3(3xm,4H,$H_{II}$, $H_{VI}$), 1.45(b,9H$(CH_3)_3$), 1.0-0.85(m, 6H,$CH(CH_3)_2$).

c) Bromo-N—(N-BOC-valyl)-piperidin-3-ol 0.5 g of $Ph_3PBr_2$ in 10 ml of $CH_2Cl_2$ are treated with 0.289 g of 3,4-epoxy-N—(N-BOC-(R)-valyl-1,2,5,6-tetrahydropyridine in 10 ml of $CH_2Cl_2$. The mixture obtained is poured onto a mixture of ice/$NaHCO_3$, the organic phase is separated, washed, dried and solvent is evaporated. A mixture of 4(R*)-bromo-N—(N-BOC-(R)-valyl)-piperidin-3(R*)-ol (COMPOUND A) and 4(S*)-bromo-N—(N-BOC-(R)-valyl)-piperidin-3 (S*)-ol (COMPOUND B) is obtained and separated by chromatography.

COMPOUND A: $^1$H-NMR: Rotameres:5.2(m,1H,N HCHCO),4.3(t,1H,NHCHCO,J=6.5 Hz), 4.25 (m,1H,$H_{IV}$), 3.88(m,1H,$H_{III}$),2.4,1.85(2xm,2H,$H_V$),1.43(b,9H$(CH_3)_3$), 0.98,0.92(2xd,6H, $CH(CH_3)_2$,J=7 Hz).

COMPOUND B: $^1$H-NMR: Rotameres: 5.25(d,1H,N HCHCO,J=6.7 Hz), 4.45(m,1H,NHCHCO), 4.15(m,1H, $H_{IV}$), 3.75(m,1H,$H_{III}$), 2.55, 2.3(2xm,2H,$H_V$), 1.9(m,1H,C H$(CH_3)_2$), 1.42 (b,9H $(CH_3)_3$), 0.9(m,6H,$CH(CH_3)_2$).

d) 3-Acetoxy-4-bromo-N—(N-BOC-valyl)-piperidine 0.57 g of bromo-N—(N-BOC-valyl)-piperidin-3-ol, dissolved in pyridine, is treated with 0.4 ml of acetic acid anhydride, the mixture obtained is stirred and a mixture of 3(R*)-acetoxy-4(R*)-bromo-N—(N-BOC-(R)-valyl)-piperidine (COMPOUND A) and 3(S*)-acetoxy-4(S*)-bromo-N—(N-BOC-(R)-valyl)-piperidine (COMPOUND B) is obtained and is separated by chromatography.

COMPOUND A: $^1$H-NMR ($d_6$-DMSO, 350 K): 6.4(b, 1H,NHCHCO), 4.73(dt,1H,NHCHCO, J=3.9 Hz,J=7.7 Hz), 4.38(dt,1H,$H_{III}$,J=4.4 Hz,J=8.8 Hz), 4.18(m,1H,NHCHCO), 4.05, 3.8, 3.35(3m,4H,$H_{II}$,$H_{VI}$), 2.3(s,3H,OCOCH_3), 1.38(s, 9H$(CH_3)_3$), 0.85(d,6H,$CH(CH_3)_2$,J=7 Hz).

COMPOUND B: $^1$H-NMR ($d_6$-DMSO, 350 K): 6.5(b, 1H,NHCHCO), 4.72(dt,1H,$H_{IV}$,J=4.0 Hz, J=7.7 Hz), 4.38(dt, 1H,$H_{III}$,J=4.4 Hz,J=8.6 Hz), 4.2(m,1H,NHCHCO),4.11, 3.78, 3.3(3m,4H,$H_{II}$,$H_{VI}$), 2.3(s,3H,OCOCH_3), 1.37(s,9H, $(CH_3)_3$), 0.85(d,6H,$CH(CH_3)_2$,J=7 Hz).

e) 3-Acetoxy-N—(N-BOC-(R)-valyl)-1,2,3,6-tetrahydropyridine 1.684 g of 3-acetoxy-4-bromo-N—(N-BOC-valyl)-piperidine dissolved in 4 ml of toluene are treated with 4 ml of DBU in a sealed tube and heated to 90°. The mixture obtained is treated with EE, extracted with aqueous HCl, washed and from the organic phase obtained solvent is evaporated. 3-Acetoxy-N—(N-BOC-(R)-valyl)-1,2,3,6-tetrahydropyridine is obtained.

$^1$H-NMR: Rotameres/Diast: 5.95, 5.85, 5.25, 5.15(4xm, 2H,$H_{IV}$,$H_V$), 4.51, 4.4(2xdd, 1H, NHCHCO,J=5.2 Hz,J=9 Hz), 4.45, 4.15(2xd,1H,$H_{VI}$,J=15.2 Hz), 3.4, 3.2(2xdd,1H, $H_{VI}$, J=3.5 Hz),2.02,2.0, 1.95(3xs,3H,OCOCH_3), 1.35(s,9H, $(CH_3)_3$), 0.85(m,6H,$CH(CH_3)_2$).

f) N—(N-BOC-(R)-valyl)-1,2,3,6-tetrahydropyridin-3-ol 0.254 g of 3-acetoxy-N—(N-BOC-(R)-valyl)-1,2,3,6-tetrahydropyridine, dissolved in 5 ml of EtOH are treated with 2N ethanolic NaOH under ice-cooling. To the mixture obtained acetic acid is added in order to neutralize the reaction mixture and solvent is evaporated. The evaporation residue obtained is mixed with $CHCl_3$, the mixture obtained is washed with NaCl-solution, the organic phase is dried and solvent is evaporated. N—(N-BOC-(R)-valyl)-1,2,3,6-tetrahydropyridin-3-ol is obtained. $^1$H-NMR: 5.9(m,2H,$H_{IV}$, $H_V$), 4.51, 4.45(2xdd,1H, NHCHCO,J=5.2 Hz,J=9.0 Hz), 1.4 (b,9H,$(CH_3)_3$), 0.9(m,6H,$CH(CH_3)_2$).

EXAMPLE D

Methylaminoacetylmutilin 13.33 g of 22-O-tosylpleuromutilin in 350 ml of EtOH are treated with 5 ml $CH_3NH_2$ (33% solution in EtOH), the mixture obtained is refluxed for ca. 30 hours and from the mixture obtained solvent is evaporated. The evaporation residue is treated with EE and the mixture obtained is extracted with 0.1N HCl. The aqueous phase obtained is treated with $NaHCO_3$ and extracted with EE. The organic phase obtained is dried and solvent is evaporated. Methylaminoacetylmutilin is obtained. $^1$H-NMR: AB-system: $v_A$=3.32,$v_B$=3.22(2H,$H_{22}$, $J_{22,NCH3}$=15 Hz), 2.42(s,3H,$CH_3NH$).

EXAMPLE E

N-BOC-1,2,5,6-tetrahydropyridine 1.66 g of 1,2,5,6-tetrahydropyridine in 25 ml of $CH_2Cl_2$ are treated with 2.02 g of N-methyl-morpholine. To the mixture obtained 4.36 g of $(BOC)_2O$ in 30 ml of $CH_2Cl_2$ are added and the mixture obtained is left for reaction for ca. 36 hours. The mixture obtained is subjected to aqueous extraction, the organic phase is dried and evaporated. N-BOC-1,2,5,6-tetrahydro-pyridine is obtained. $^1$H-NMR: 5.82(m,1H,$H_{IV}$), 5.64(m,1H,$H_{III}$), 3.86(b,2H,$H_{II}$), 3.47(t,2H,$H_{VI}$), 2.12(b,1H, $H_V$), 1.46(m,9H,$(CH_3)_3$).

EXAMPLE F

3,4-Epithio-N(N-BOC-valyl)-piperidine 2.91 g of KSCN in 3 ml of $H_2O$ are added to a mixture of 5.96 g of 3,4-epoxy-N—(N-BOC-valyl-1,2,5,6-tetrahydropyridine in 10 ml of absolute EtOH and the mixture obtained is stirred for 72 hours at RT. The mixture obtained is subjected to aqueous extraction, the solvent of the organic phase obtained is evaporated and the evaporation residue is subjeted to chromatography. 3,4-Epithio-N(N-BOC-(R)-valyl)-piperidine is obtained. Melting point: 69.71°

The invention claimed is:

1. A compound of formula

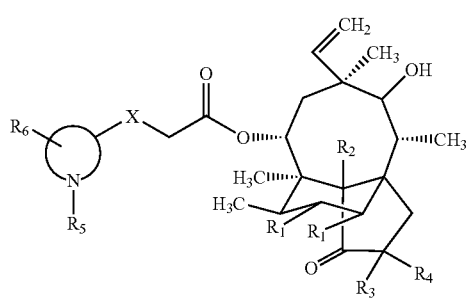

I wherein
  $R_1$ and $R_1'$ are hydrogen or deuterium,
  $R_2$, $R_3$ and $R_4$ are hydrogen or deuterium,
  $R_5$ is the residue of an alpha amino acid, wherein the N which is part of the ring in formula I is acylated by the carboxylic group of said amino acid and wherein the carbonyl group of said amino acid is bound to the nitrogen of the group of formula

and the —OH group of said amino acid function is missing,

X is S or N-ALK, the group of formula is piperidinyl or tetrahydropyridinyl,
ALK is $(C_{1-4})$alkyl, and
$R_6$ is hydrogen, hydroxy or $(C_{2-12})$acyloxy,
with the proviso that if the group is piperidinyl and X is S, then $R_6$ is other than hydrogen.

2. A compound according to claim 1 which is selected from the group consisting of
  14-O-[4-hydroxy-N-valyl-piperidin-3-yl]-sulfanylacetyl-mutilin,
  14-O-[3-hydroxy-N-valyl-piperidin-4-yl]-sulfanylacetyl-mutilin,
  14-O-[3-hydroxy-N-histidinyl-piperidin-4-yl]-sulfanylacetylmutilin,
  14-O-[3-hydroxy-N-valyl-piperidin-4-yl]-methylaminoacetylmutilin,
  14-O-[4-hydroxy-N-valyl-piperidin-3-yl]-methylaminoacetylmutilin,
  14-O—[N-valyl)-1,2,3,6-tetrahydropyridin-3-yl]-sulfanylacetylmutilin, and
  14-O—[N-valyl)-1,4,5,6-tetrahydropyridin-4-yl]-sulfanylacetylmutilin.

3. A compound of formula

II wherein
  $R_1$ and $R_1'$ are hydrogen or deuterium,
  $R_2$, $R_3$ and $R_4$ are hydrogen or deuterium,
  $R_7$ is a protecting group or the residue of an alpha amino acid, wherein the N which is part of the ring in formula II is acylated by the carboxylic group of said amino acid and wherein the carbonyl group of said amino acid is bound to the nitrogen of the group of formula

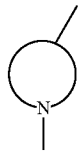

and said amino acid function is devoid of the —OH group, and wherein the amino group is protected, X is S or N-ALK, the group of formula

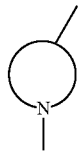

is piperidinyl or tetrahydropyridinyl,

ALK is $(C_{1-4})$alkyl, and $R_8$ is hydrogen, hydroxy or $(C_{2-12})$acyloxy, with the proviso that if the group of formula

is piperidinyl and X is S, then $R_8$ is other than hydrogen.

4. A compound according to claim 3 selected from the group consisting of
14-O—[N-BOC-4-hydroxy-piperidin-3-yl]-sulfanylacetylmutilin,
14-O—[N-BOC-3-hydroxy-piperidin-4-yl]-sulfanylacetylmutilin,
14-O-[4-hydroxy-N-BOC-piperidin-3-yl]-methylaminoacetylmutilin,
14-O-[3-hydroxy-N-BOC-piperidin-4-yl]-methylaminoacetylmutilin,
14-O—[N-BOC-1,4,5,6-tetrahydropyridin-4-yl]-sulfanylacetylmutilin,
14-O-[4-hydroxy-N—(N-BOC-valyl)-piperidin-3-yl]-sulfanylacetylmutilin,
14-O-[3-hydroxy-N—(N-BOC-valyl)-piperidin-4-yl]-sulfanylacetylmutilin,
14-O-[4-acetoxy-N—(N-BOC-valyl)-piperidin-3-yl]-sulfanylacetylmutilin,
14-O-[3-acetoxy-N—(N-BOC-valyl)-piperidin-4-yl]-sulfanylacetylmutilin,
14-O-[3-hydroxy-N—(N-BOC-histidinyl)-piperidin-4-yl]-sulfanylacetylmutilin,
14-O-[3-hydroxy-N—(N-BOC)-valyl-piperidin-4-yl]-methylaminoacetylmutilin,
14-O-[4-hydroxy-N—(N-BOC)-valyl-piperidin-3-yl]-methylaminoacetylmutilin,
14-O—[N—(N-BOC-valyl)-1,4,5,6-tetrahydropyridin-4-yl]- sulfanylacetylmutilin,
14-O—[N—(N-BOC-valyl)-1,2,3,6-tetrahydropyridin-3-yl]- sulfanylacetylmutilin.

5. A compound of claim 1 in the form of a salt.

6. A pharmaceutical composition comprising a compound of claim 1 in association with at least one pharmaceutical excipient.

7. A pharmaceutical according to claim 6 further comprising another pharmaceutically active agent.

8. A method of treatment of microbial diseases comprising administering to a subject in need of such treatment an effective amount of a compound of claim 1.

* * * * *

UNITED STATES PATENT AND TRADEMARK OFFICE
CERTIFICATE OF CORRECTION

PATENT NO. : 7,612,103 B2 Page 1 of 1
APPLICATION NO. : 10/521926
DATED : November 3, 2009
INVENTOR(S) : Heinz Berner et al.

It is certified that error appears in the above-identified patent and that said Letters Patent is hereby corrected as shown below:

On the Title Page, first column at item (30) Foreign Application Priority Data, at the third item delete "PCT/EP03/08059" and insert -- PCT/EP03/03215 --.

Signed and Sealed this

Fifth Day of January, 2010

David J. Kappos
*Director of the United States Patent and Trademark Office*